United States Patent
Ui et al.

(10) Patent No.: US 9,468,698 B2
(45) Date of Patent: Oct. 18, 2016

(54) GAS PROCESSING APPARATUS

(71) Applicant: KABUSHIKI KAISHA TOSHIBA, Tokyo (JP)

(72) Inventors: Akio Ui, Tokyo (JP); Yosuke Sato, Kanagawa (JP); Masato Akita, Kanagawa (JP); Yasushi Sanada, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/633,745

(22) Filed: Feb. 27, 2015

(65) Prior Publication Data
US 2015/0265740 A1 Sep. 24, 2015

(30) Foreign Application Priority Data
Mar. 24, 2014 (JP) .................. 2014-060064

(51) Int. Cl.
*A61L 9/16* (2006.01)
*A61L 9/22* (2006.01)

(51) Int. Cl.
*B01D 53/32* (2006.01)
*B01D 53/86* (2006.01)

(52) U.S. Cl.
CPC .. *A61L 9/16* (2013.01); *A61L 9/22* (2013.01); *B01D 53/323* (2013.01); *B01D 53/869* (2013.01); *B01D 53/8631* (2013.01); *A61L 2209/212* (2013.01); *B01D 2251/104* (2013.01); *B01D 2255/802* (2013.01);
(Continued)

(58) Field of Classification Search
CPC ..... A61L 9/16; A61L 9/22; A61L 2209/212; B01D 53/323; B01D 53/8631; B01D 53/869; B01D 2251/104; B01D 2257/406; B01D 2257/702; B01D 2257/708; B01D 2257/90; B01D 2255/802; B01D 2259/818; Y10T 156/1052; Y10T 156/10
See application file for complete search history.

(56) References Cited

U.S. PATENT DOCUMENTS

| 2005/0118079 A1* | 6/2005 | Muroi et al. ............... 422/186.3 |
| 2005/0179395 A1* | 8/2005 | Pai ........................... 315/111.21 |
| 2005/0249646 A1 | 11/2005 | Iwama et al. |

(Continued)

FOREIGN PATENT DOCUMENTS

| JP | 2005-515843 | 6/2005 |
| JP | 2005-342708 | 12/2005 |

(Continued)

OTHER PUBLICATIONS

Corke et al.; "Dielectric Barrier Discharge Plasma Actuators for Flow Control", Annu. Rev. Fluid Mech.,42, pp. 505-529, (2010).

*Primary Examiner* — Xiuyu Tai
(74) *Attorney, Agent, or Firm* — Finnegan, Henderson, Farabow, Garrett & Dunner LLP

(57) ABSTRACT

A gas processing apparatus of an embodiment includes: first and second dielectric substrates facing with each other; first and second discharge electrodes respectively disposed on a pair of facing principal surfaces of the dielectric substrates; first and second ground electrodes respectively disposed on a pair of principle surfaces at opposite sides of the principle surfaces of the dielectric substrates; a gas flow path to supply gas to be processed between the discharge electrodes; an AC power source to generate first and second plasma-induced flows by applying an AC voltage between the discharge electrodes and the ground electrodes; and a region disposed between the dielectric substrates at downstream of the plasma-induced flows from the discharge electrodes, and a gap between the dielectric substrates being 1.3 times or less of a sum of thicknesses of the plasma-induced flows.

11 Claims, 12 Drawing Sheets

(52) U.S. Cl.
CPC .. *B01D 2257/406* (2013.01); *B01D 2257/702* (2013.01); *B01D 2257/708* (2013.01); *B01D 2257/90* (2013.01)

(56) References Cited

U.S. PATENT DOCUMENTS

2008/0063577 A1  3/2008  Crowe et al.
2008/0193343 A1* 8/2008  Vezzu ................. 422/186.18
2012/0315194 A9  12/2012  Rousseau et al.
2013/0064710 A1  3/2013  Jacob

FOREIGN PATENT DOCUMENTS

| JP | 2008-289801 | 12/2008 |
|----|-------------|---------|
| JP | 2010-532253 | 10/2010 |

* cited by examiner

GAS PROCESSING APPARATUS

CROSS-REFERENCE TO RELATED APPLICATION

This application is based upon and claims the benefit of priority from Japanese Patent Application No. 2014-060064, filed on Mar. 24, 2014; the entire contents of which are incorporated herein by reference.

FIELD

Embodiments described herein relate generally to a gas processing apparatus.

BACKGROUND

There is a case when hazardous substances, malodorous substances, and so on are contained in atmospheric gas in a life space, a refrigerator, a warehouse, and so on and exhaust gas from a process unit. A small-sized gas decomposition device (including an air cleaning device, an air cleaning air conditioner, and a gas purifying device) decomposing, sterilizing, and so on (hereinafter, to be referred to as gas decomposition) these hazardous substances, malodorous substances, and so on with high efficiency has been required.

Generally, in the gas decomposition device, decomposition object gas is introduced into a gas decomposition chamber by a blower, and is decomposed and purified by discharge, a decomposition catalyst, a photocatalyst, or radical (ozone and so on).

Besides, a technology in which process object gas is blown to a purification processing means by using a plasma actuator is also disclosed.

However, it is not necessarily easy in the gas decomposition device to decompose hardly decomposable gas at high speed.

In the gas decomposition device, improvement in a gas decomposition ratio means a process of a large gas flow rate and a large gas decomposition reaction rate. These are described below.

A) Large Flow Rate Process

A gas decomposition method by a catalyst is simple and easy, and frequently used. However, this method uses an adsorption and decomposition reaction of gas by a reaction at a catalyst surface. Accordingly, when a surface area is not enough large relative to a gas flow path, it becomes difficult to secure a reaction rate. At this time, a fine-meshed catalyst-carrying filter is used to increase the surface area. As a result, a pressure loss becomes large and it is difficult to enable a large flow rate. To overcome the pressure loss, a large amount of blowing is necessary to incur large-sizing of a device, increase in price, and increase in power consumption. Further, periodical exchange of filters become necessary to resolve clogging.

In case of the photocatalyst, a reaction occurs only at a surface where light is irradiated, and therefore, both an arrival of the decomposition object gas to the surface and the light irradiation are required, and it is difficult to enlarge decomposition efficiency. Besides, a large surface area to enable the above becomes necessary, and the device becomes large.

The gas decomposition by discharge uses a decomposition reaction in a gas phase. However, a discharge range in an atmospheric pressure, for example, a discharge range of a needle electrode is very small such as approximately 1 mm or less of a tip part of the needle. Accordingly, it is necessary to densely dispose an electrode group to avoid undecomposition caused by passing over of gas. As a result, the pressure loss becomes large, and a large-capacity and large-sized blower becomes necessary to enable the large flow rate.

Namely, in a general gas decomposition device, the gas decomposition ratio and the pressure loss are in a trade-off relationship. Therefore, a large-sized device becomes necessary to enable the large flow rate of gas decomposition process. Namely, a small-sizing of the device becomes difficult, and the exchange of filter becomes necessary.

B) Large Gas Decomposition Reaction Rate

The gas decomposition reaction rate is determined by an amount of chemical species which causes the decomposition and a reaction rate (when the gas decomposition is performed by an oxidation reaction, an amount of oxidant and an oxidation reaction rate (oxidation potential)). Ozone is easy to be generated by discharge, a high density supply is possible, in addition, a lifetime is long, and therefore, it is often used for the gas decomposition process. Ozone is effective for decomposition of ammonia and formaldehyde gas. However, ozone is in short of an oxidizing power for decomposition of hardly decomposable gas (for example, toluene and acetaldehyde gas). Therefore, it is difficult to decompose the hardly decomposable gas at high speed even if ozone is supplied in high concentration.

OH radical, O radical having active oxygen have much stronger oxidizing power, and are able to decompose the hardly decomposable gas at high speed. However, reactivities of OH radical and O radical are high, and therefore, lifetimes thereof are short, and it is difficult to supply them in high density to the decomposition object gas.

There is a method in which a reactant is held at a filter, a mesh, and so on to increase the chemical species incurring the decomposition. However, diffusion and supply of the object gas to the surface is also necessary in this method, and as a result, it is difficult to enable approximation and reaction of the oxidant and the object gas in bulk.

DETAILED DESCRIPTION

A gas processing apparatus of an embodiment includes: a first and a second dielectric substrate facing with each other; a first and a second discharge electrode respectively disposed on a pair of facing principal surfaces of the dielectric substrates; a first and a second ground electrode respectively disposed on a pair of principle surfaces at opposite sides of the principle surfaces of the dielectric substrates; a gas flow path configured to supply gas to be processed between the discharge electrodes; an AC power source configured to generate a first plasma-induced flow at a first discharge electrode side and a second plasma-induced flow at a second discharge electrode side by applying an AC voltage between the first discharge electrode and the first ground electrode and between the second discharge electrode and the second ground electrode to ionize the gas; and a region disposed between the dielectric substrates at downstream of the plasma-induced flows from the discharge electrodes, and a gap between the dielectric substrates being 1.3 times or less of a sum of thicknesses of the plasma-induced flows.

Hereinafter, embodiments are described in detail with reference to the drawings.

First Embodiment

Figure 1:
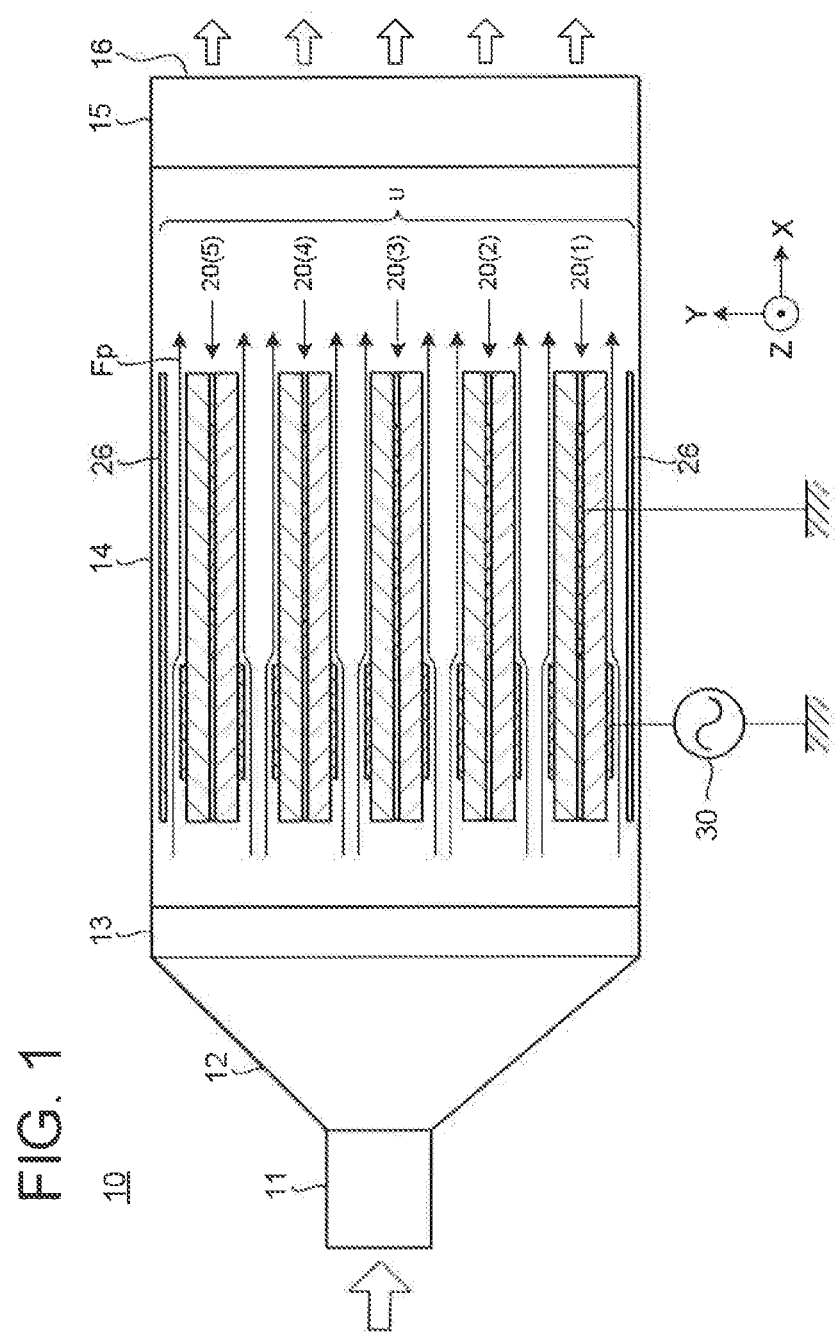
FIG. 1 is a side view illustrating an overall configuration of a gas decomposition device 10 according to a first embodiment.

FIG. 1 illustrates an overall configuration of a gas decomposition device 10 according to a first embodiment.

In the gas decomposition device 10, decomposition object gas (gas containing at least either of carbon or nitrogen, for example, formaldehyde, toluene, acetaldehyde, ammonia gas) contained in an atmosphere or process exhaust gas is decomposed by discharge generated by an AC high voltage applied between a discharge electrode and a ground electrode. The gas decomposition device 10 functions as a gas processing apparatus processing gas.

The gas decomposition device 10 includes a gas inlet port 11, a flow path enlarging part 12, a prefilter 13, a gas decomposition chamber 14, an ozone process chamber 15, and a gas outlet port 16, and insides of these are gas flow space.

The gas containing the decomposition object gas is introduced into the gas inlet port 11.

The flow path enlarging part 12 enlarges a flow path from the gas inlet port 11 to the prefilter 13, the gas decomposition chamber 14. The flow path enlarging part 12 is a gas flow path configured to supply the gas between discharge electrodes 22 (or between the discharge electrode 22 and a gas flow partition 26).

The prefilter 13 removes dust, mote, and so on in the gas flowing in the gas decomposition chamber 14.

In the gas decomposition chamber 14, a process unit U including plural gas decomposition elements 20 (1) to 20 (5) is disposed to process the gas. Note that a detail of the process unit U is described later.

The ozone process chamber 15 includes an ozone processor (not-illustrated. For example, an ozone catalyst), and processes and decomposes ozone gas in high concentration, NOx, or SOx generated at the gas decomposition chamber 14.

The gas containing the decomposed decomposition object gas flows out of the gas outlet port 16.

The gas is introduced from the gas inlet port 11, passes through the prefiter 13, the gas decomposition chamber 14 (the process unit U), and the ozone process chamber 15, and is exhausted from the gas outlet port 16.

Figure 2:
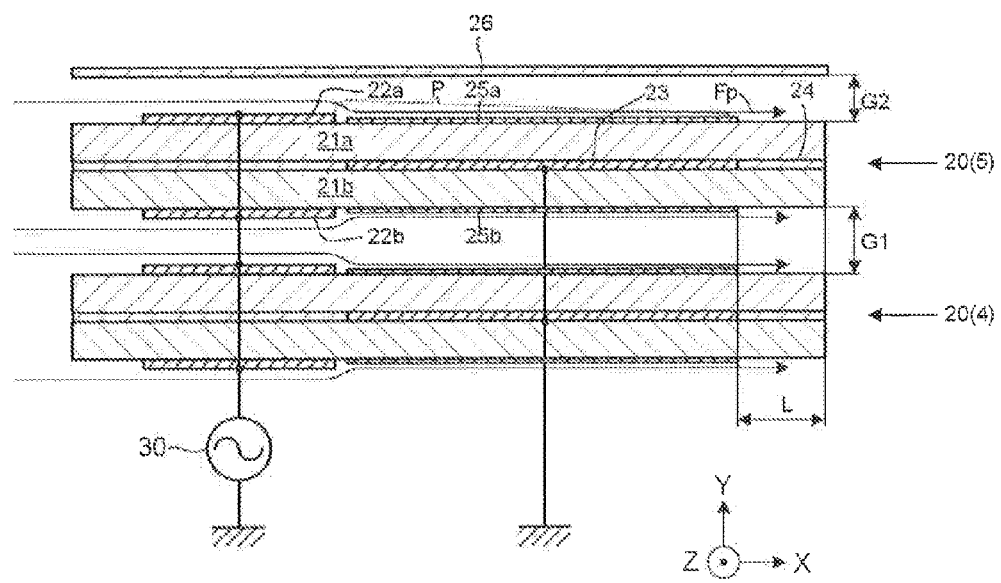
FIG. 2 is an enlarged schematic view illustrating a detail of gas decomposition elements 20 constituting a process unit U.

FIG. 2 enlargedly illustrates details of the gas decomposition elements 20 constituting the process unit U.

The process unit U includes the gas decomposition elements 20 (20 (1) to 20 (5)) and the gas flow partition 26. Here, the number of gas decomposition elements 20 included in the process unit U is set to be five, but this can be appropriately changed.

The gas decomposition element 20 includes dielectric substrates 21 (21a, 21b), discharge electrodes 22 (22a, 22b), a ground electrode 23, an insulating sealing layer 24, photocatalyst layers 25 (25a, 25b), and the gas flow partition 26.

The dielectric substrate 21 is a substrate of a dielectric material (for example, quartz, silicon rubber, and Kapton (a polyimide)). For example, a quartz plate with a thickness of 1 mm can be used as the dielectric substrate 21.

The discharge electrode 22, the ground electrode 23 are each made up of an electric conductor of metal and so on. For example, it is possible to form a thin film of gold (Au) on the dielectric substrate 21 by using sputtering or by plating to be the discharge electrode 22 and the ground electrode 23.

The dielectric substrates 21 of adjacent gas decomposition elements 20 are disposed with a gap G1.

The dielectric substrate 21 of the gas decomposition element 20 at an uppermost part (and a lowermost part) is disposed to have a gap G2 with the gas flow partition 26. Note that, here, a thickness of the discharge electrode 22 and a thickness of the photocatalyst 25 are neglectable relative to the gaps G1, G2.

The discharge electrodes 22 (22a, 22b), the ground electrode 23, the dielectric substrates 21 (21a, 21b) are, for example, respectively 2 mm×30 mm, 10 mm×30 mm, and 20 mm×50 mm in a length direction (X direction), and in a depth (Z direction). Besides, the gaps G (G1, G2) are for example, each 2 mm. As a result, the gas decomposition chamber 14 (the process unit U) is able to be reduced in size to be, for example, 20 mm×30 mm×50 mm.

The insulating sealing layer 24 is to suppress a reverse discharge at the ground electrode 23. For example, a silicon oxide film, an induced insulating film, an insulating silicone filler, or a kapton tape coating can be used as the insulating sealing layer 24.

When gas is in contact with the ground electrode 23, a flow of a later-described plasma-induced flow Fp is suppressed or abnormal discharge (overheat) may occur at a minute space by a backflow resulting from the reverse discharge. To prevent the above, it is desirable to closely seal a periphery of the insulating sealing layer 24 by the insulating sealing layer 24.

The photocatalyst layers 25a, 25b are layers of a photocatalyst material (for example, $TiO_2$), and are disposed in a vicinity of plasma P or in the plasma P on the dielectric substrate 21. The photocatalyst layers 25a, 25b are able to be formed by, for example, a coating of the photocatalyst material.

The photocatalyst layers 25a, 25b are activated by light emission from the plasma P, and remove NOx and so on contained in the plasma P. Namely, it is possible to improve a gas decomposition ratio combined with the plasma P in itself and the gas decomposition by the photocatalyst.

Note that the gas decomposition element 20 may not have the photocatalyst layer 25. However, when the gas composition element 20 has the photocatalyst layer 25, the decomposition of gas can be further accelerated.

A high voltage AC power source 30 applies an AC high voltage (for example, a sinusoidal voltage of 10 kHz, 6 kV) between the discharge electrodes 22a, 22b and the ground electrode 23.

Here, the adjacent dielectric substrates 21 are disposed to face with the gap G1.

Besides, the gas flow partitions 26 are each disposed to face the dielectric substrates 21 at the uppermost layer and the lowermost layer with the gap G2.

As described below, the gap G1 is 1.3 times or less of a sum of thicknesses h of the plasma-induced flows Fp on a pair of facing dielectric substrates 21 (G1≤1.3*2h=2.6h). Specifically, the gap G1 is preferably 2 mm or more and 8 mm or less. To increase a decomposition efficiency of hardly decomposable gas, it is more preferable to set the gap G1 to be 2 mm or more and 6 mm or less, and to satisfy "G1≤1.0*2h".

The gap G2 is 1.3 times or less of the thickness h of the plasma-induced flow Fp on the dielectric substrate 21 (G2≤1.3*h). Specifically, the gap G2 is preferably 1 mm or more and 4 mm or less. To increase the decomposition efficiency of the hardly decomposable gas, it is more preferable to set the gap G2 to be 1 mm or more and 3 mm or less, and to satisfy "G2≤1.0*h".

The gaps G1, G2 are set as stated above, and thereby, it is possible to effectively make use of active oxygen (OH radical, O radical) in the plasma P, and to efficiently decompose the decomposition object gas.

Figure 3:
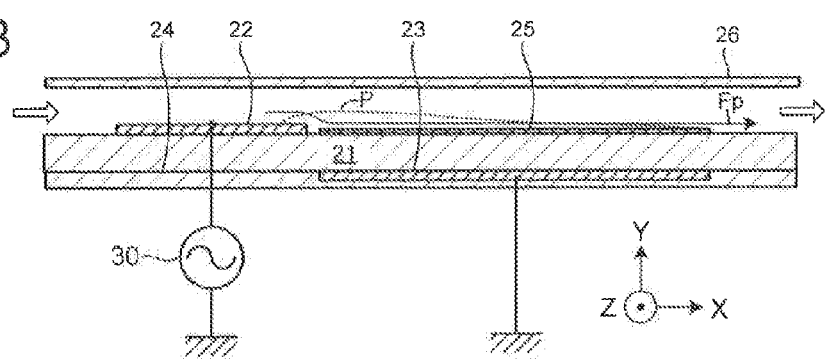
FIG. 3 is an enlarged side view conceptually illustrating an operation state of the gas composition element 20.

FIG. 3 conceptually illustrates an operation state of the gas composition element 20.

The plasma P is generated on a surface of the dielectric substrate 21 in a ground electrode 23 direction at the discharge electrode 22 side by the AC high voltage from the high voltage AC power source 30. The plasma P contains positive ions and electrons. The positive ions flow from the discharge electrode 22 toward a surface direction of the dielectric substrate 21 on the ground electrode 23. This flow collides with atmosphere, a gas flow is accompanied at a periphery thereof, and the plasma-induced flow Fp is generated.

The electrons are accumulated on a surface of the dielectric substrate 21 which is in contact with the plasma P to be charged up to negative. Accordingly, the positive ions averagely flow in the surface direction of the dielectric substrate 21 which corresponds from the discharge electrode 22 to the ground electrode 23. The generated plasma P is a thin surface plasma, and therefore, the plasma-induced flow Fp also becomes a surface flow flowing in a vicinity of the dielectric substrate 21. Namely, the ground electrode 23 is disposed to be shifted in the X direction relative to the discharge electrode 22, and thereby, the plasma-induced flow Fp flowing in the X direction is generated.

Figure 4:
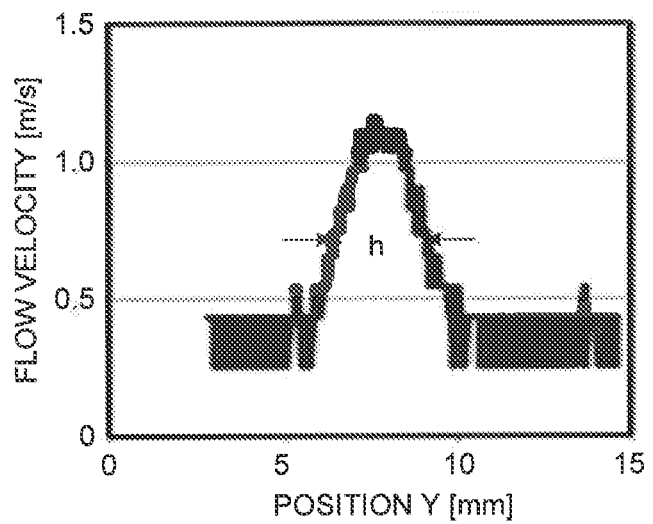
FIG. 4 is a graphic chart illustrating a distribution of a flow rate V of a plasma-induced flow Fp.

FIG. 4 is a graphic chart illustrating a distribution of a flow rate V of the plasma-induced flow Fp.

A horizontal axis is a position Y in a longitudinal direction of the dielectric substrate 21, and a position of Y=6 mm corresponds to the surface of the dielectric substrate 21. A hot-wire air flow meter is moved up and down, and the distribution of the flow rate V of the plasma-induced flow Fp is measured. Here, a sinusoidal voltage with a frequency f of 10 kHz, and an applied voltage Vrf of 6 kV is applied.

As illustrated in FIG. 4, the plasma-induced flow Fp flows only in the vicinity of the surface (approximately a half value width (thickness) h=2.4 mm) of the dielectric substrate 21. Namely, the plasma-induced flow Fp with the thickness h of 2.4 mm is generated.

Figure 5:
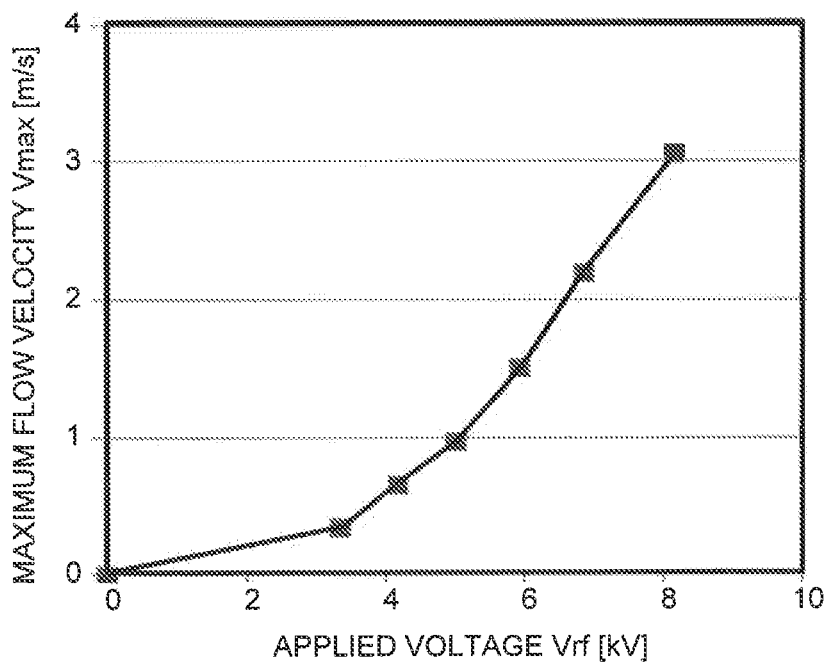
FIG. 5 is a graphic chart illustrating applied voltage Vrf dependence at a maximum flow rate Vmax of the plasma-induced flow Fp.

FIG. 5 is a graphic chart illustrating dependence on the applied voltage Vrf at a maximum flow rate Vmax of the plasma-induced flow Fp.

As illustrated in FIG. 5, the plasma-induced flow Fp is generated from the applied voltage Vrf of approximately 3 kV. A density (ion density) of the plasma becomes higher and an attracting electric filed becomes larger as an increase of the applied voltage Vrf. Accordingly, the flow rate V of the plasma-induced flow Fp becomes large as the increase of the applied voltage Vrf.

The plasma-induced flow Fp is generated on the discharge electrode 22 without generating a flow (pressure) from outside by using a blower such as a fan. As stated above, the gaps G1 and G2 are small. Therefore, the gas sucked from upstream passes inside the plasma P.

The frequency f and the applied voltage Vrf are able to be appropriately changed within ranges of 2 kHz to 200 kHz, 3 kV to 15 kV respectively. As particularly preferable ranges, the frequency f and the applied voltage Vrf can be set at 5 kHz to 20 kHz, 5 kV to 10 kV respectively. The frequency f and the applied voltage Vrf are changed as stated above, then the thickness h of the plasma-induced flow Fp changes within a range of 1.5 mm to 3 mm. As a result, the gaps G1, G2 are respectively able to be appropriately set within ranges of, for example, 2 mm to 8 mm, 1 mm to 4 mm.

Next, a gas decomposition mechanism is described. Parts of the atmosphere and the decomposition object gas are decomposed by discharge.

Active oxygen (hydroxy radical: OH, oxygen atom radical: O, ozone: $O_3$ and so on) are generated from oxygen gas ($O_2$), moisture ($H_2O$) in the atmosphere and hydrogen, nitrogen, and an oxygen component in the decomposition object gas.

When the decomposition object gas (for example, formaldehyde, toluene, acetaldehyde, ammonia gas) is mixed with oxidant, they are decomposed into $CO_2$, $H_2O$, NOx ($NO_2$, NO) and so on by reactions represented by (1), (2), (3).

Note that NOx is able to be removed by the photocatalyst layers 25a, 25b and the ozone process chamber 15 provided at a subsequent stage.

Decomposition object gas+OH→$CO_2$+$H_2O$+NO$x$ (1)

Decomposition object gas+O→$CO_2$+$H_2O$+NO$x$ (2)

Decomposition object gas+$O_3$→$CO_2$+$H_2O$+NO$x$ (3)

An oxidation potential Vo by a major oxidant (active oxygen), a reaction rate Vr [$cm^3$/molecules] with toluene gas at a temperature of 198 [K], and a lifetime Ls of the active oxygen in the atmosphere are illustrated in Table.

TABLE

| | OXIDATION POTENTIAL Vo [V] | REACTION RATE Vr [$cm^3$/molecules] | LIFETIME IN ATMOSPHERE Ls [s] |
|---|---|---|---|
| OH | 2.8 | $6 \times 10^{-12}$ | about $10^{-4}$ |
| O($^1$D) | 2.2 | $1.3e^{-13}$ | about $10^{-3}$ |
| $O_3$ | 2.07 | $1.2e^{-20}$ | about $10^{-3}$ |
| $H_2O_2$ | 1.78 | — | — |
| $F_2$ | 3.03 | — | — |
| $Cl_2$ | 1.36 | — | — |

As illustrated in Table, the oxidation potentials Vo of the active oxygen are OH>O>>$O_3$, and a gas decomposition capability relative to the decomposition object gas is large and the reaction rate is large in this sequence. Namely, in case of the gas easy to be decomposed such as formaldehyde and ammonia gas, the high-speed and high efficient decomposition is enough possible by $O_3$.

However, toluene and acetaldehyde are the hardly decomposable gas. For example, in case of the toluene gas, as illustrated in Table, the reaction rates of the oxidant and the toluene gas (under room temperature (298 [K])) are in a sequence of "$O_3$<O<OH". The decomposition rate of toluene and so on by $O_3$ is very small, and it is substantially seldom decomposed.

On the other hand, the lifetime Ls largely changes in accordance with a reactivity, and the lifetimes Ls of the oxidant in the atmosphere are in a sequence of "$O_3$>>O>OH". OH and O are highly active, and therefore, their lifetimes are very short. When a flow rate of 10 [m/s] is assumed, only approximately 1 mm, 10 mm of OH and O survive respectively at a downstream of the plasma P. As a result, when the gas decomposition in the gas phase by the oxidant at the downstream of the plasma-induced flow Fp is considered, collisions of OH and O with decomposition object gas molecules are small, and the decomposition becomes difficult. The lifetime of $O_3$ is long (for several dozen minutes), and therefore, the decomposition reaction occurs because $O_3$ enough collides with the decomposition object gas even at downstream. Note that it is energetically difficult for $O_3$ to react with the hardly decomposable gas.

In the present embodiment, as illustrated in FIG. 2, the other dielectric substrate 21 or the gas flow partition 26 is disposed to face the dielectric substrate 21. Accordingly, the plasma-induced flow Fp (or a flow including a flow of the gas and the blowing by the fan) passes inside the plasma P. Therefore, OH and O radicals having short lifetimes and the decomposition object gas (contained in the gas) are reacted at the plasma P (or in the vicinity thereof), and the decomposition object gas is decomposed with high efficiency.

Here, the gas which passes through the plasma P (the surface plasma) becomes the plasma-induced flow Fp (the thickness h) to flow downstream. When the gap G is set to be larger than the thickness h, a flow of the gas is also generated in which the gas does not pass inside the plasma P but passes upward of the plasma P. As a result, the gas decomposition rate Vr by the gas decomposition element 20 is lowered.

Hereinafter, dependence on the gap G of the gas decomposition rate Vr is described.

Figure 6:
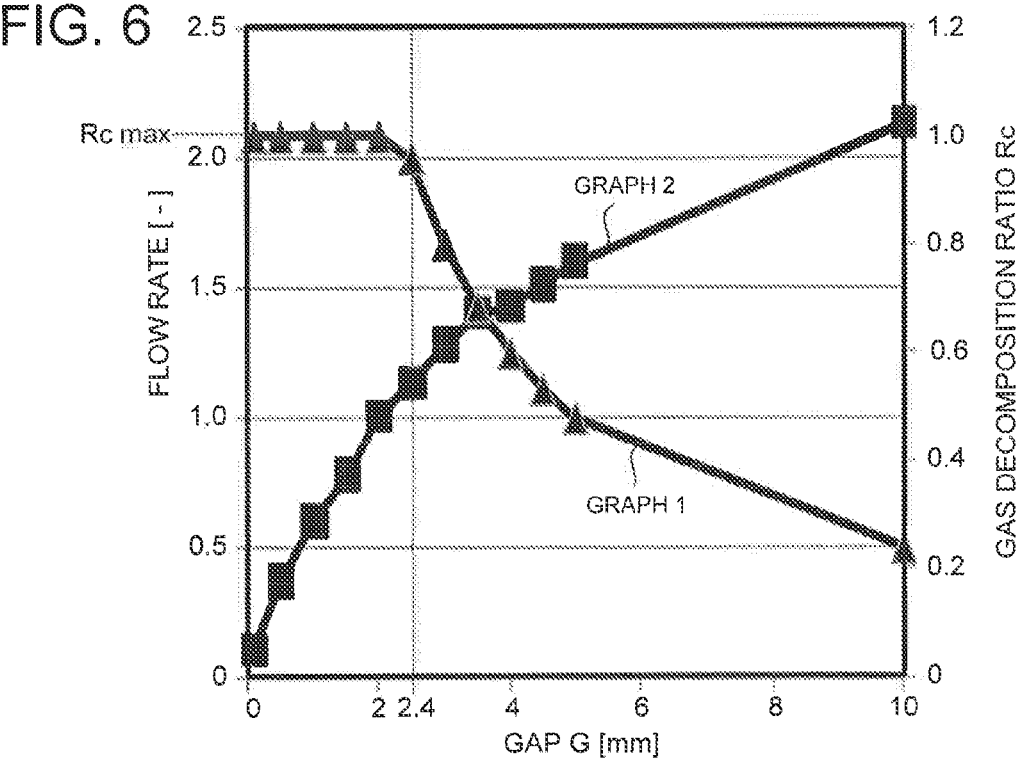
FIG. 6 is a graphic chart illustrating a correspondence among a gap G, a gas decomposition ratio Rc, and a flow rate Q.
Figure 7:
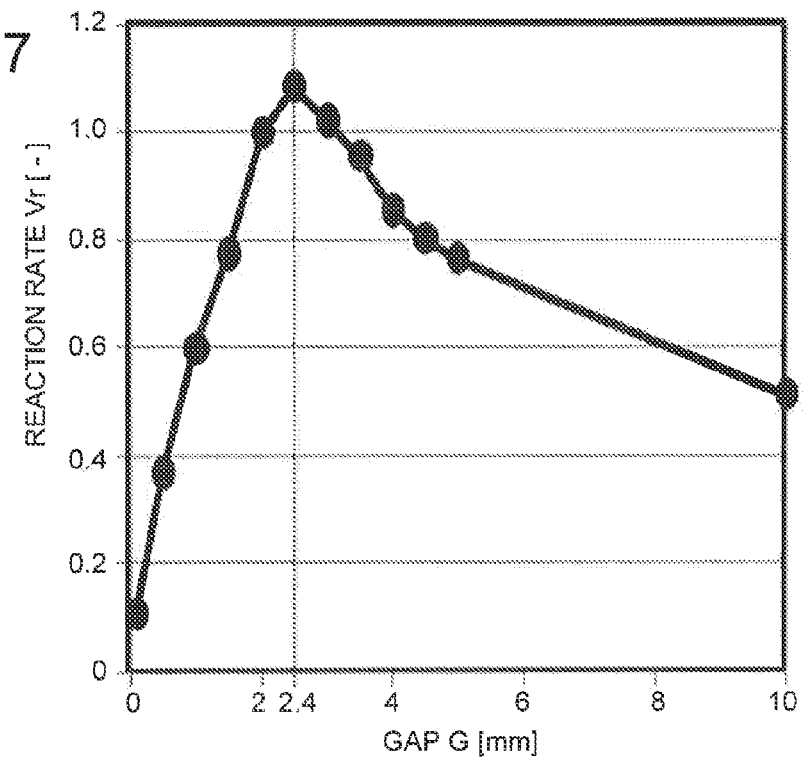
FIG. 7 is a graphic chart illustrating a correspondence between the gap G and a gas decomposition rate Vr.

A graph 1 in FIG. 6 illustrates a correspondence between the gap G and the gas decomposition ratio Rc. A graph 2 in FIG. 6 illustrates a correspondence between the gap G and a flow rate Q of the plasma-induced flow Fp. Besides, FIG. 7 illustrates a correspondence between the gap G and the reaction rate Vr.

When the gas decomposition ratio Rc is calculated, the applied voltage Vrf is set to be 8.5 kV, and the flow rate Q of the gas is set to be 0.025 $m^3$/min. Besides, the thickness h of the plasma-induced flow Fp is set to be 2.4 mm.

Besides, the gas passing through the thickness h of the plasma-induced flow Fp is assumed to be perfectly mixed with the plasma P.

As illustrated in the graph 1 in FIG. 6, a gas flow passing outside the plasma P increases when the gap G2 is larger than the thickness h, and the gas decomposition ratio Rc is remarkably lowered. When the gap G2 is 1.3 times of the thickness h or less, the decomposition ratio of 3/4 or more of a maximum gas decomposition ratio Rcmax is secured. Namely, it is important to set the gap G2 to be 1.3 times or less of the thickness h. On the other hand, the gap G1 is set to be 2.6 times or less of the thickness h of the plasma-induced flow Fp.

Besides, when the gap G becomes narrow, the flow rate Q decreases resulting from the pressure loss. When this effect is estimated from the pressure loss between flat plates (the dielectric substrates 21), the result becomes as illustrated in the graph 2 in FIG. 6. Note that a conductance data in "Vacuum Handbook" edited by ULVAC, Inc. is used, and it is normalized by the flow rate Q when the gap G is 2 mm.

FIG. 7 illustrates a correspondence between the gap G and a one pass decomposition rate Vr. A gas decomposition rate by one pass represents the gas decomposition rate when the gas passes through the gas decomposition device 10 (the process unit U) only for one time.

The gas decomposition rate Vr is determined by a multiplication of the gas decomposition ratio Rc and the flow rate Q. Namely, the gas decomposition rate Vr become the maximum at the gap G which is equal to the thickness h of the plasma-induced flow. Besides, the gas decomposition rate Vr is secured to be a value from the maximum to approximately 3/4 or more when the gap G is within a range of ±30% of the thickness h.

Gas decomposition operations when the process unit U illustrated in FIG. 1 is used are described. The process unit U having a basic configuration as illustrated in FIG. 1, FIG. 2 is used, and thereby, it is possible to exchange the gas flow partitions 26 at other than the uppermost layer and the lowermost layer into the dielectric substrates 21, and to suppress a stacking width of the process unit U into small. As a result, it is possible to generate the plasma-induced flow Fp with large flow rate by the small-sized process unit U.

Figure 8:
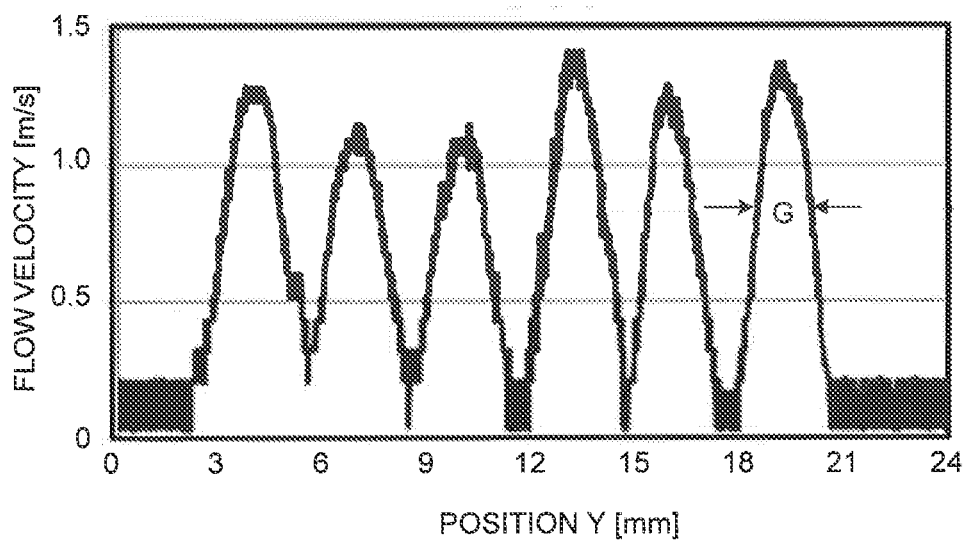
FIG. 8 is a graphic chart illustrating a distribution of the flow rate V of the plasma-induced flow Fp.

FIG. 8 is a graphic chart illustrating the distribution of the flow rate V of the plasma-induced flow Fp. As same as FIG. 4, the hot-wire air flow meter is moved up and down, and the distribution of the flow rate V of the plasma-induced flow Fp is measured. Here, a sinusoidal voltage of 10 kHz, 6 kV is applied. The gap G1 between the dielectric substrates 21 and the gaps G2 between the uppermost and lowermost dielectric substrates 21 and the gas flow partitions 26 are each set to be 2 mm.

As illustrated in FIG. 8, six flow paths of stable plasma-induced flows Fp are observed at a width corresponding to the gaps G1, G2 (=2 mm).

Figure 9:
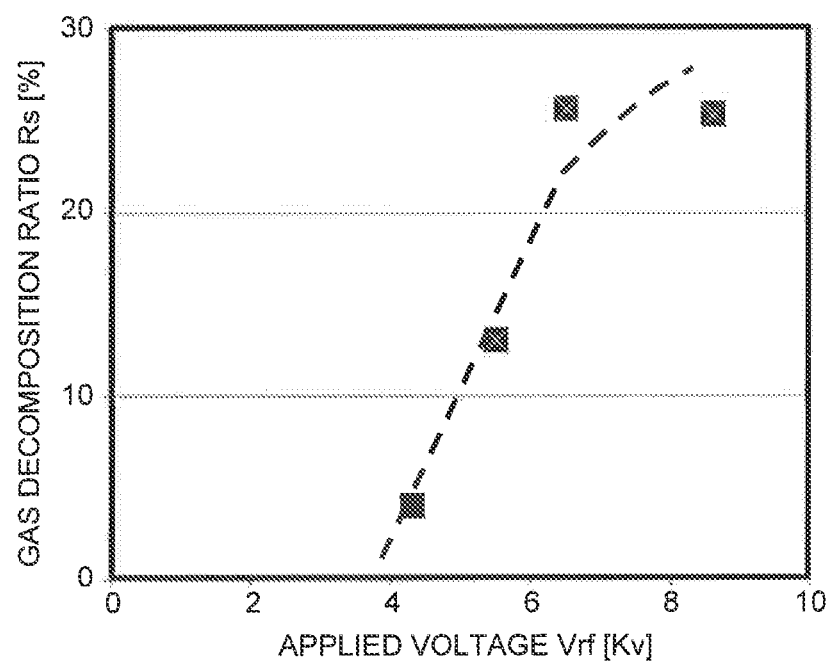
FIG. 9 is a graphic chart illustrating applied voltage Vrf dependence of a gas decomposition ratio Rs.

FIG. 9 is a graphic chart illustrating dependence on the applied voltage Vrf of the gas decomposition ratio Rs by one pass of the toluene gas. Here, in FIG. 1, the atmosphere containing the toluene gas at 50 ppm concentration is supplied from the gas inlet port 11 as the gas to be processed.

The gas passing through the gas decomposition elements 20 is sampled, and the concentration of the toluene gas is measured by the FT-IR. The applied voltage Vrf is set to be approximately 4 kV, and thereby, the plasma P is generated. The gas decomposition ratio Rs increases as the increase of the applied voltage Vrf, and the gas decomposition ratio Rs becomes approximately 28% when the applied voltage Vrf is 8.5 kV.

Namely, though the gap G1 is set to be a narrow gap of 2 mm, the flow rate Q=0.025 [m³/min] is enabled in a fanless.

As stated above, the decomposition reaction rate of toluene is very large because the toluene gas is highly efficiently decomposed by a direct collision of the toluene gas with OH, O radicals generated at the plasma P.

Figure 10:
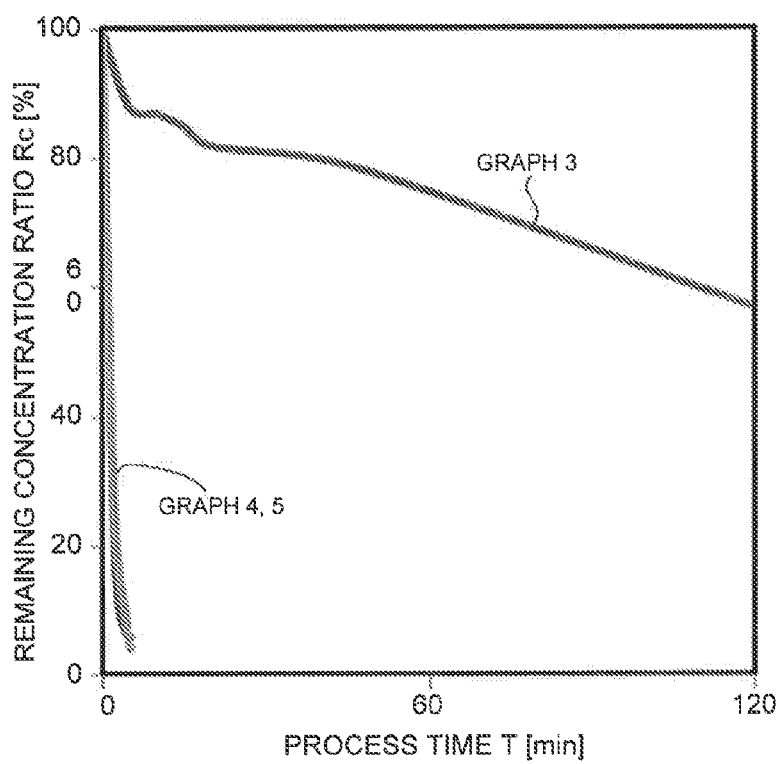
FIG. 10 is a graphic chart illustrating a gas decomposition/removal performance of a gas decomposition device using plasma generation ozone.
Figure 11:
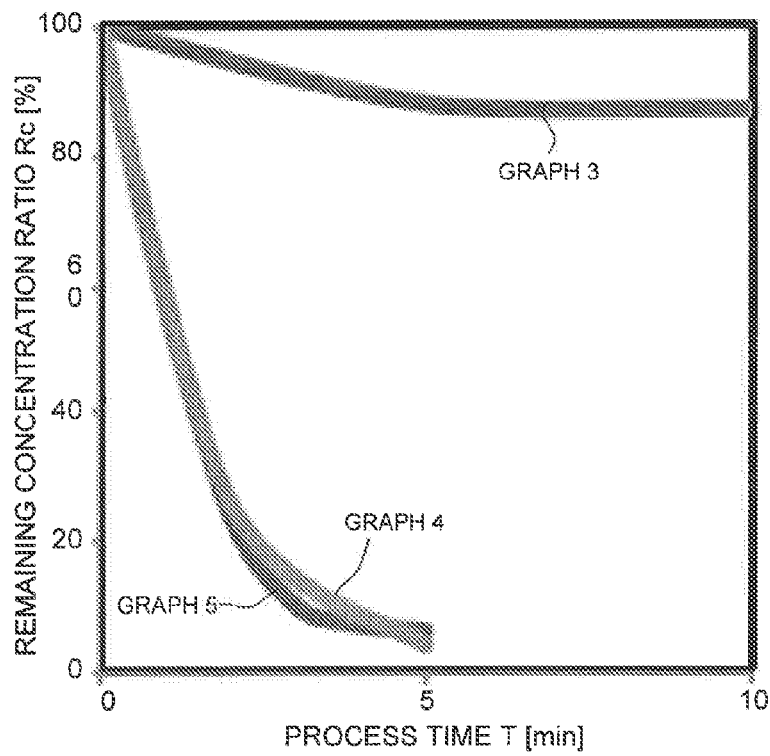
FIG. 11 is a graphic chart illustrating the gas decomposition/removal performance of the gas decomposition device using plasma generation ozone.

FIG. 10, FIG. 11 are views illustrating a gas decomposition and removal performance of a commercially available large-sized deodorizing device, being a gas decomposition device using plasma generation ozone as an example. Graphs 3, 4, 5 respectively correspond to toluene, formaldehyde, and ammonia. FIG. 11 is a view enlarging a part of FIG. 10.

Here, an initial concentration is set at 100 to be normalized. Measurements are performed under a condition of a hermetic space of 1 m³, and a flow rate of 2.5 m³/min. A device size is 415 mm×239 mm×555 mm. The gases which are easy to be decomposed and removed such as ammonia, formaldehyde can be removed in a few minutes, but as for the toluene gas, a half quantity cannot be removed even after two hours.

Here, when a decomposition ratio of toluene by a first-order reaction is estimated for comparison with the present embodiment, the gas decomposition ratio Rc by one pass is approximately 0.3% (the flow rate: 2.5 [m³/min]).

Figure 12:
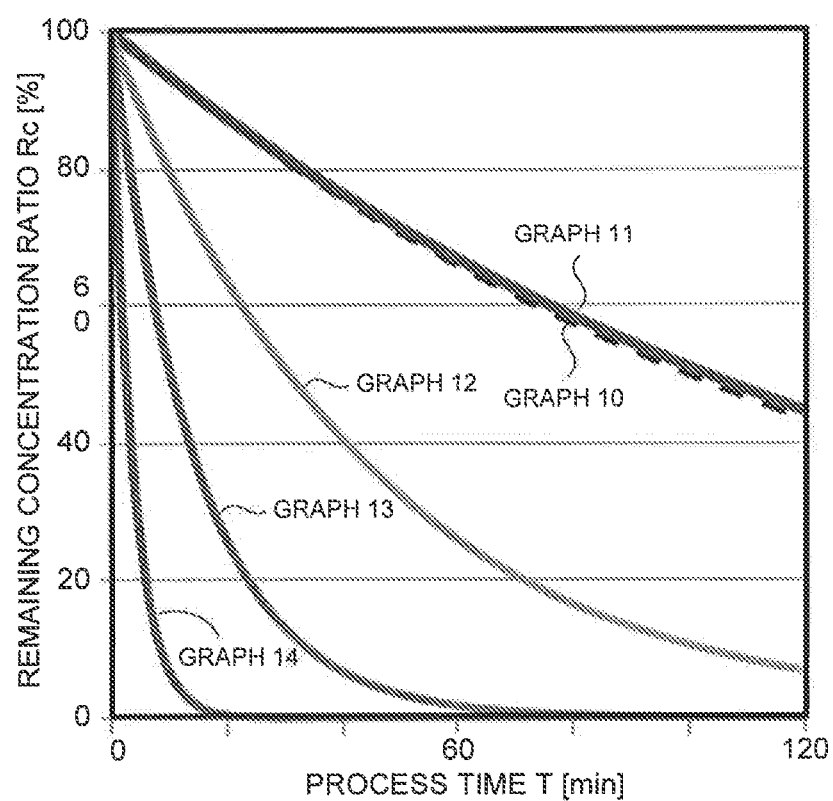
FIG. 12 is a graphic chart illustrating decomposition time characteristics of toluene.

A decomposition time characteristic of toluene calculated from the above-stated experimental results is illustrated in FIG. 12. Graphs 11 to 14 illustrate the one pass decomposition ratios Rc (remaining concentration ratio) by the gas decomposition device 10 of the present embodiment, and a graph 10 illustrates the one pass decomposition ratio Rc by the commercially available large-sized deodorizing device as a comparative example. In the graph 11, Z axis direction lengths of the discharge electrode 22 and the ground electrode 23 and the number of stages of the gas decomposition elements 20 are respectively set to be 30 mm and 5 stages. On the other hand, in the graphs 12 to 14, the Z axis direction lengths of the discharge electrode 22 and the ground electrode 23 and the number of stages of the gas decomposition elements 20 are respectively set to be 100 mm and 5 stages, 200 mm and 10 stages, and 300 mm and 20 stages.

Here, a variation per hour of the toluene concentration when the gas decomposition device 10 is operated in the hermetic space of 1 m³ is found. Note that the normalization is performed while setting the initial concentration at 100 as same as FIG. 10 and FIG. 11.

As described above, the gas decomposition device 10 of the present embodiment has approximately 100 times of one pass decomposition ratio compared to the commercially available large-sized deodorizing device (28% to 0.3%). A flow rate ratio between the gas decomposition device 10 and the commercially available large-sized deodorizing device is 1/100, and therefore, as illustrated in the graphic charts 10, 11, they have approximately the same toluene removal performance.

Besides, the gas decomposition device 10 has a fanless configuration, and a volume size thereof is (1/6)×(1/4)×(1/5) to be approximately 1/100 or less of the commercially available large-sized deodorizing device.

The flow rate of the plasma-induced flow Fp in itself is determined by the applied voltage and the gaps G (G1, G2) of the flow path. Accordingly, the gas flow rate at the gas decomposition device 10 of the present embodiment is able to be increased by increasing the Y direction (the number of stages) and the Z direction (the depth direction). At this time, the decomposition ratio of the gas which passes through does not change.

Even in case of 300 mm and 20 stages as illustrated in the graph 14, the process unit U has a volume of 200 mm×400 mm×150 mm to be approximately 1/5 of the commercially available large-sized deodorizing device, and it is possible to remove the hardly decomposable gas such as the toluene gas within approximately a few minutes to 10 minutes.

Namely, according to the present embodiment, it is possible to drastically enable to reduce the size of the process unit U owing to the large gas decomposition reaction. Further, the areas of the discharge electrode 22 and the ground electrode 23 are increased, and thereby, the small-sized and drastically highly-efficient gas decomposition becomes possible.

Besides, the fan may be set to increase the gas flow rate at the upstream and the downstream of the discharge electrode 22 and the ground electrode 23, or at the downstream of the photocatalyst layer 25. Also in this case, the pressure loss is relaxed and overcome by the plasma-induced flow Fp.

As stated above, in the present embodiment, the AC high voltage is applied between the discharge electrode 22 and the ground electrode 23 sandwiching the dielectric substrate 21 therebetween to thereby generate the dielectric barrier discharge, and the plasma-induced flow Fp flowing in the vicinity of the surface of the dielectric substrate 21 is induced.

In the present embodiment, a pair of dielectric substrates 21 are disposed to face to correspond to the thickness h of the plasma-induced flow Fp. Accordingly, it becomes easy to draw the gas into the thin plasma (the surface plasma) P. As a result, the highly active OH radical, O radical having short lifetime which are generated in the plasma P react with the decomposition object gas in high-speed.

Besides, the pressure loss between the pair of dielectric substrates 21 becomes very small owing to the existence of the plasma-induced flow Fp. Namely, it is possible to provide the gas decomposition device 10 which has a large flow rate, though it is small-sized, and with high efficiency. Besides, the fanless is also possible, and the gas decomposition device 10 is further small-sized.

Modification Example of First Embodiment

Figure 13:
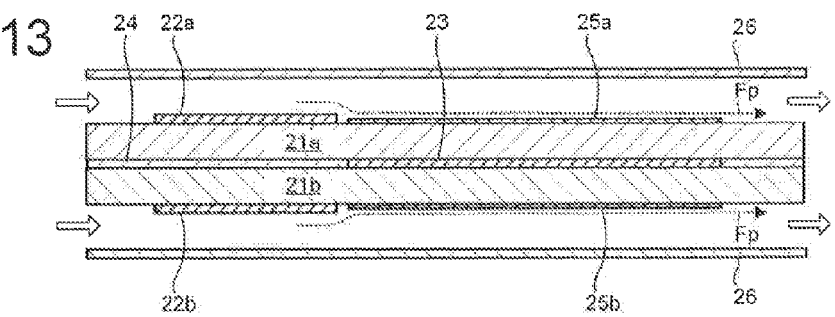
FIG. 13 is a side view illustrating the process unit U according to a modification example 1.

FIG. 13 is a schematic view illustrating the process unit U according to a modification example 1 of the first embodiment. In this process unit U, the gas flow partitions 26 respectively face a pair of connected dielectric substrates 21a, 21b. As stated above, the dielectric substrate 21 and the gas flow partition 26 are disposed to face, then the dielectric substrates 21 are not necessarily disposed to face directly.

Figure 14:
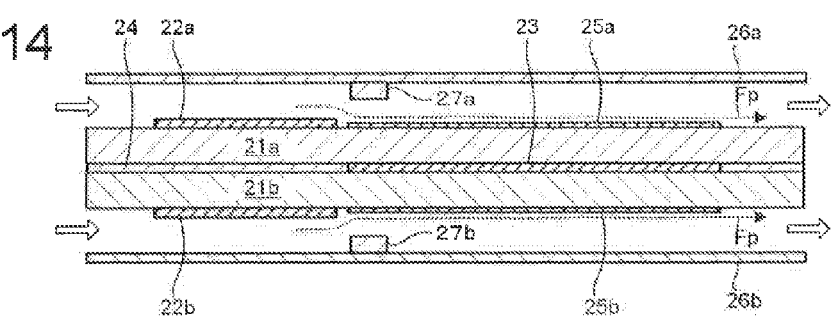
FIG. 14 is a side view illustrating the process unit U according to a modification example 2.

FIG. 14 is a schematic view illustrating a process unit U according to a modification example 2 of the first embodiment. Projecting parts (obstacles) 27a, 27b to turn the flow of the gas downstream are disposed on the gas flow partitions 26 at a downstream side (a right side in the drawing) than the discharge electrode 22. As a result, the more flow of the gas passes inside the plasma P, and the gas decomposition ratio improves.

Figure 15:
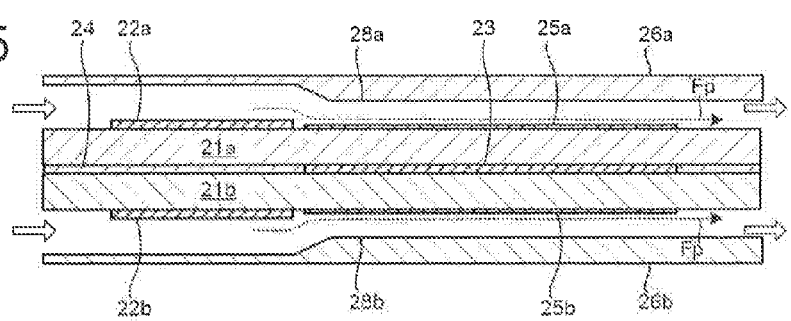
FIG. 15 is a side view illustrating the process unit U according to a modification example 3.

Besides, FIG. 15 is a schematic view illustrating the process unit U according to a modification example 3 of the first embodiment. The gas flow partitions 26 have a taper shape to narrow down the flow path toward the ground electrode 23 side at the downstream side than the discharge electrodes 22.

Figure 16:
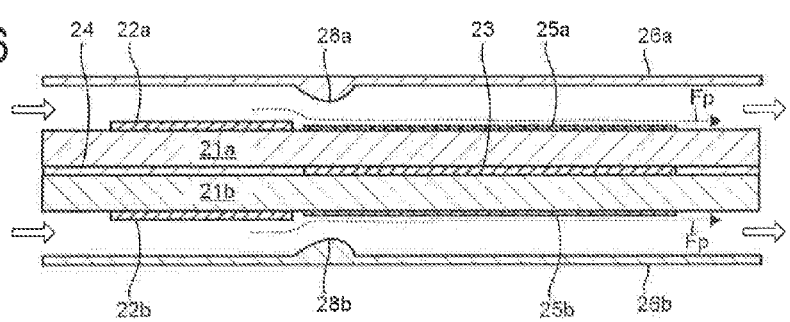
FIG. 16 is a side view illustrating the process unit U according to a modification example 4.

Further, FIG. 16 is a schematic view illustrating the process unit U according to a modification example 4 of the first embodiment. After the flow path is narrowed down, it opens again. As a result, the pressure loss according to the narrowed gap G is reduced, and the increase in the flow rate becomes possible. Namely, it is possible to enable both the highly efficient gas decomposition and the increase in the flow rate.

Figure 17:
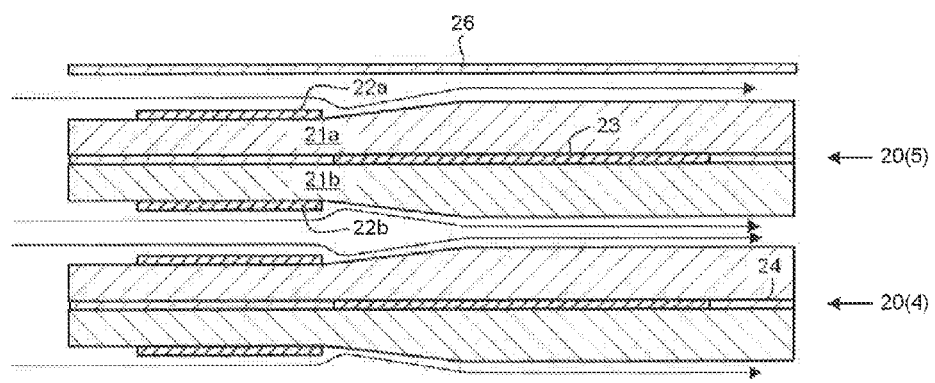
FIG. 17 is a side view illustrating the process unit U according to a modification example 5.

On the other hand, FIG. 17 is a schematic view illustrating the process unit U according to a modification example 5 of the first embodiment. Here, the flow path between the dielectric substrates 21 disposed to face has the taper-shape (the gap G1 between the dielectric substrates 21 becomes narrow in a direction along the plasma-induced flow Fp). Namely, the dielectric substrates 21 have the thick taper-shape at the downstream side than the discharge electrodes 22. As a result, the gas flows more inside the plasma P, and the gas decomposition ratio improves.

Figure 18:
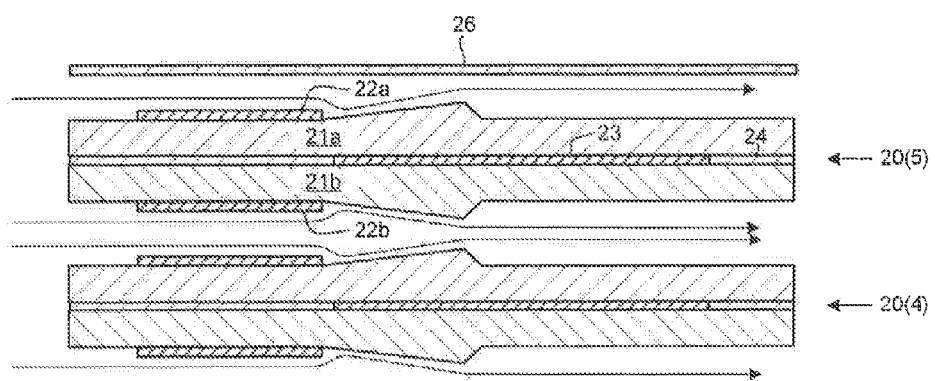
FIG. 18 is a side view illustrating the process unit U according to a modification example 6.

Further, FIG. 18 is a schematic view illustrating the process unit U according to a modification example 6 of the first embodiment. Here, the flow path between the dielectric substrates 21 disposed to face becomes wide after it becomes narrow. The flow path is opened at the downstream side than the ground electrode 23, and thereby, the pressure loss in accordance with the narrowed gap G is reduced, and the increase in the flow rate is possible.

As stated above, when the gap G1 between the dielectric substrates 21 (or the gap G2 between the dielectric substrate 21 and the gas flow partition 26) is not constant, "G1≤2.6 h" or "G2≤1.3*h" may be satisfied at a part of a region between the dielectric substrates 21 and so on.

Second Embodiment

Figure 19:
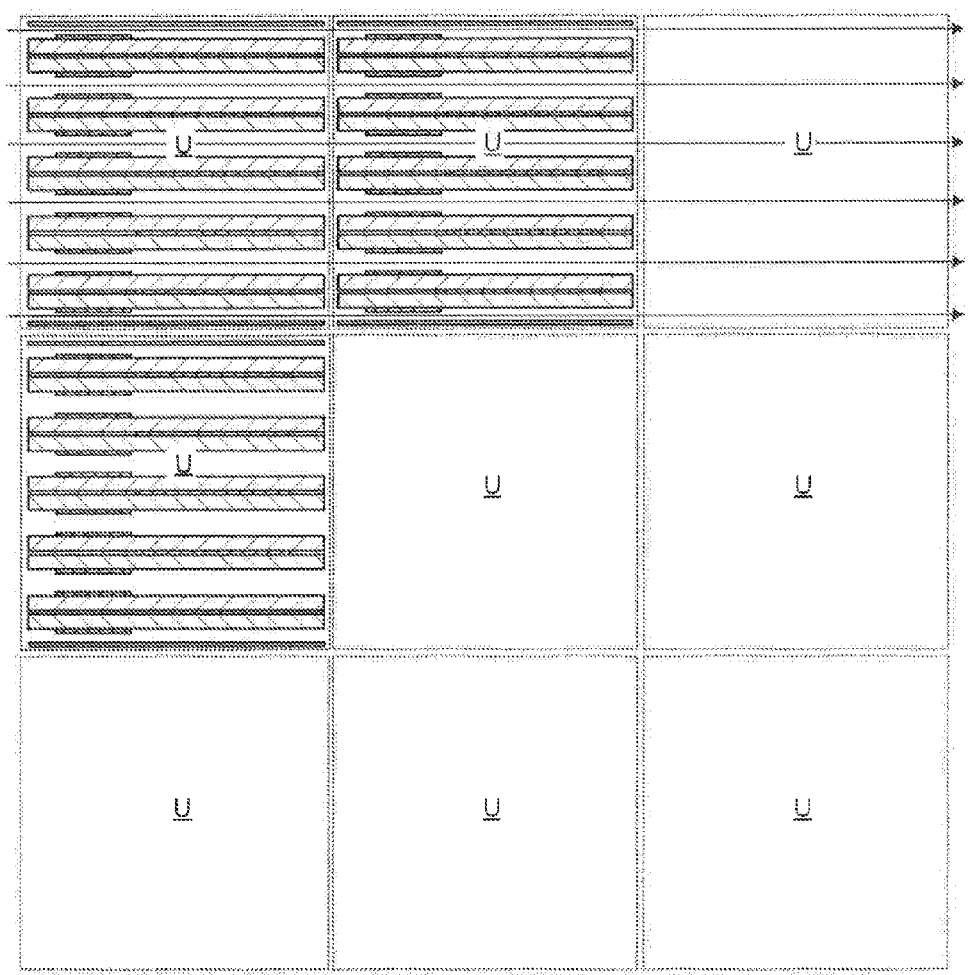
FIG. 19 is a side view illustrating an overall configuration of a gas decomposition device 10 according to a second embodiment.

FIG. 19 is a schematic view illustrating a process unit U according to a second embodiment. In this process unit U, gas decomposition elements 20 are disposed in plural to be arranged in a Y direction and an X direction (in parallel, in series).

The plural process units U (the gas decomposition elements 20) are disposed in series and in parallel as stated above, and thereby, the decomposition efficiency, the flow rate can further be improved.

Third Embodiment

Figure 20:
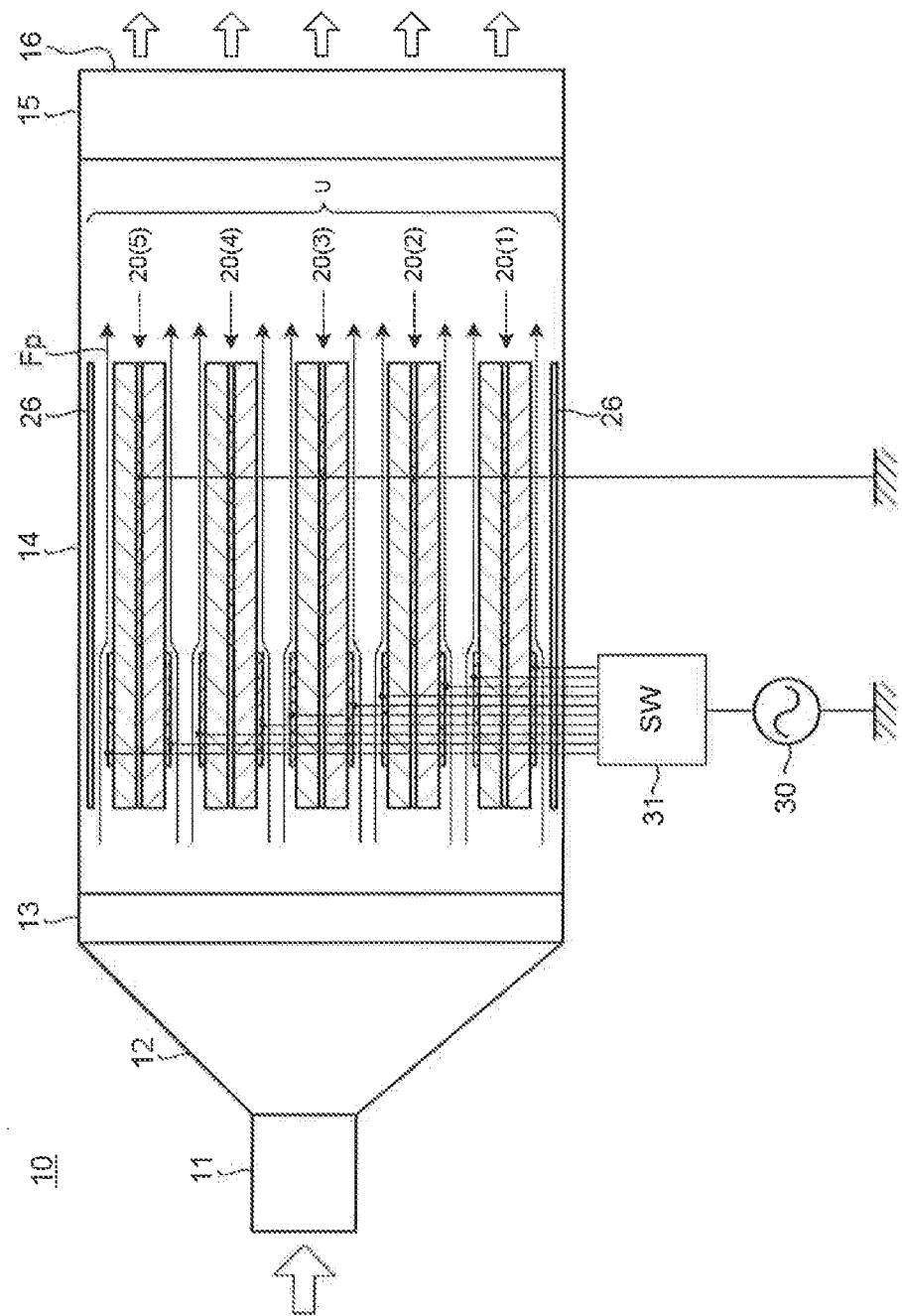
FIG. 20 is a side view illustrating an overall configuration of a gas decomposition device 10 according to a third embodiment.

FIG. 20 is a schematic view illustrating a process unit U according to a third embodiment. In this process unit U, it is possible to appropriately select discharge electrodes 22 where a high-voltage AC voltage is to be applied by using a switch 31. Namely, it is possible to apply the AC high voltage to only a part of or all of gas decomposition elements 20 according to need. It is possible to adjust the number of gas decomposition elements 20 which are to be operated in accordance with cases when a rapid gas decomposition is necessary, when a power-saving operation and a quiet operation are to be performed, when a strong-wind operation is necessary, and so on.

As an example, the high-voltage AC voltage may be applied while selecting one of or both of a group of a pair of the facing discharge electrodes 22 between the gas decomposition elements 20 (4) and 20 (5) and a group of a pair of the facing discharge electrodes 22 between the gas decomposition elements 20 (3) and 20 (4). Namely, the switch 31 is a switching mechanism applying the high-voltage AC voltage by selecting a group of the pair of the facing dielectric electrodes 22.

Besides, the discharge electrodes 22 where the high-voltage AC voltage is applied may be appropriately selected by using plural high-voltage AC voltage power sources.

The selection of the discharge electrodes 22 where the high-voltage AC voltage is applied may be performed by a unit of the gas decomposition element 20, or by a unit of the process unit U.

Fourth Embodiment

Figure 21:
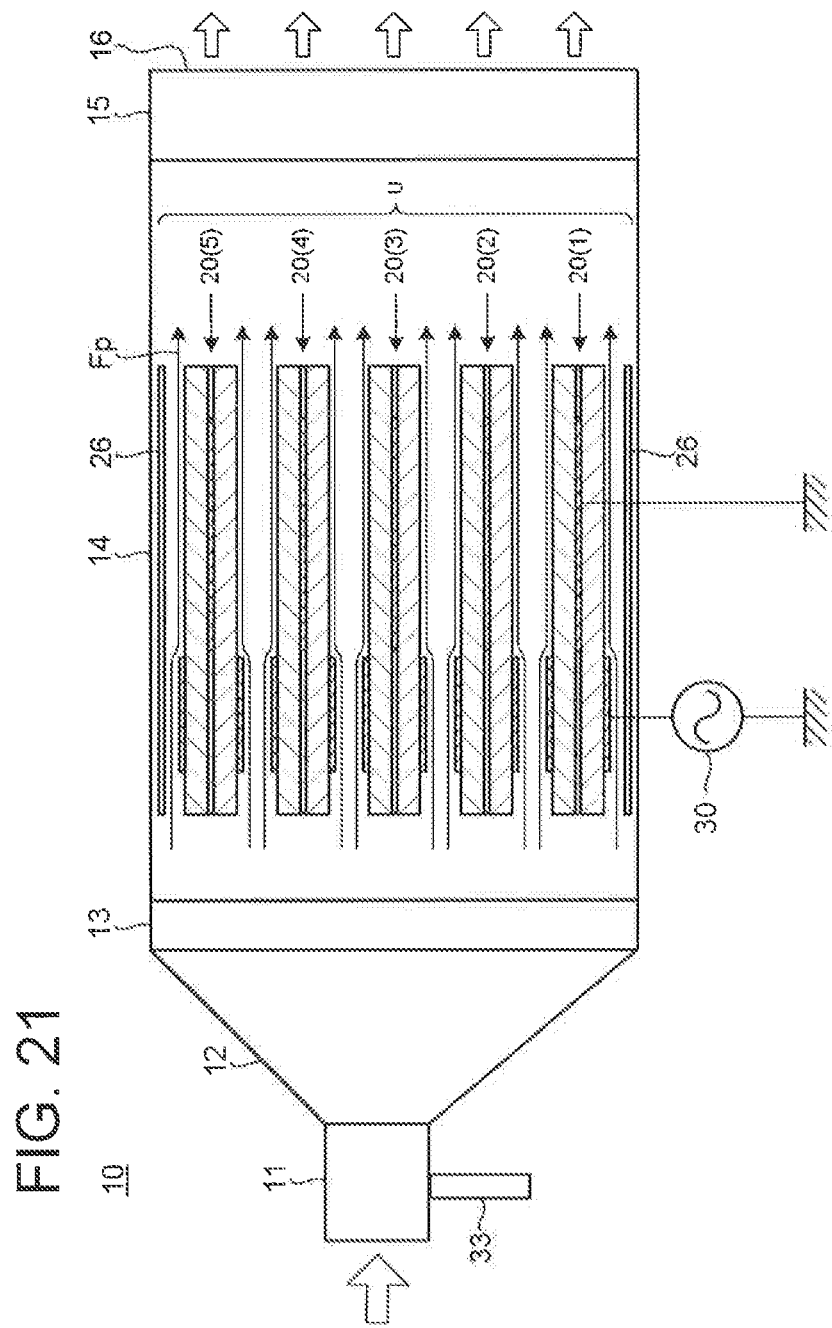
FIG. 21 is a side view illustrating an overall configuration of a gas decomposition device 10 according to a fourth embodiment.

FIG. 21 is a schematic view illustrating a gas decomposition device 10 according to a fourth embodiment.

Here, gas containing hydrogen (for example, gas containing $H_2O$ vapor) is introduced from a gas port 33 connected to a gas inlet port 11.

The gas containing hydrogen is mixed at an upstream side, and thereby, a generation amount of OH radical in a plasma P increases, and a gas decomposition ratio increases. A decomposition capability of OH radical is the highest in the oxidant using oxygen, but as stated above, the OH radical is highly active and has the short lifetime. Besides, a lot of carbon is contained in toluene ($C_5H_5$—$CH_3$), and OH of the toluene concentration or more is required to completely decompose the toluene, and a hydrogen source is in short only by hydrogen in toluene.

Here, when water vapor is introduced, a stable plasma is difficult to be ignited. Accordingly, it is conceivable that dry gas is flowed before the ignition to make a surface of the discharge electrode 22 dry, the discharge is started, and thereafter, the decomposition object gas containing the water vapor is flowed.

Further, the lifetime of OH is approximately 0.0001 seconds, and the lifetime of O is approximately 0.001 seconds to be short. Accordingly, it is important to enable the high efficient gas decomposition suppressing the pressure loss that a length L from a downstream end of the ground electrode 23 to a downstream end of the dielectric substrate 21 (refer to FIG. 2) on the dielectric substrate 21 is 0.001v or less (note that v is a gas flow rate [m/s]) (L≤0.001v). For example, under a condition of the flow rate of 5 [m/s], L≤5 mm.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gas processing apparatus, comprising:
   a first and a second dielectric substrate facing with each other;
   a first and a second discharge electrode respectively disposed on a pair of facing principal surfaces of the dielectric substrates;
   a first and a second ground electrode respectively disposed on a pair of principle surfaces at opposite sides of the principle surfaces of the dielectric substrates;
   a gas port downstream of a gas inlet port configured to add an addition gas including a hydrogen element to atmosphere, an object gas including at least one of carbon element and nitrogen element, and oxygen gas, forming a gas mixture;
   a gas flow path configured to supply the gas mixture between the first and second discharge electrodes;
   an AC power source configured to generate a first plasma-induced flow at a first discharge electrode side and a second plasma-induced flow at a second discharge electrode side by, applying an AC voltage between the first discharge electrode and the second discharge electrodes and the ground electrodes to ionize the mixture the first and the second plasma-induced flows including OH radical formed from the oxygen gas and the addition gas; and
   a region disposed between the dielectric substrates at downstream of the plasma-induced flows from the first and second discharge electrodes, and a gap between the dielectric substrates being 2 mm or more and 6 mm or less,
   wherein the object gas in the gap is decomposed by the OH radical.

2. The gas processing apparatus of claim 1,
   wherein the first and second ground electrodes are respectively disposed to be shifted in a direction relative to the first and second discharge electrodes, and the plasma-induced flows flow in the direction.

3. The gas processing apparatus of claim 1,
   wherein the gap becomes narrow in a direction along the plasma-induced flows.

4. The gas processing apparatus of claim 1,
   wherein a distance L from a downstream side end of the first ground electrode to a downstream side end of the first dielectric substrate is a product of 0.001 [sec] and a flow rate v [m/sec] of the gas mixture (0.001*v) or less.

5. The gas processing apparatus of claim 1, further comprising:
   photocatalyst layers respectively disposed on the facing principle surfaces of the dielectric substrates.

6. The gas processing apparatus of claim 1,
   wherein the addition gas is water vapor.

7. The gas processing apparatus of claim 1, further comprising:
   a third dielectric substrate disposed on the second ground electrode;
   a gas flow partition facing the third dielectric substrate;
   a third discharge electrode disposed on the third dielectric substrate, the AC power source being configured to generate a third plasma-induced flow at the third discharge electrode side by applying the AC voltage between the third discharge electrode and the second ground electrode to ionize the gas mixture, the third plasma-induced flow including OH radical; and
   a second region disposed between the third dielectric substrate and the gas flow partition at downstream of the third plasma-induced flow from the third discharge electrode, and a second gap between the third dielectric substrate and the gas flow partition being 1 mm or more and 3 mm or less,
   wherein the object gas in the second gap is decomposed by the OH radical.

8. The gas processing apparatus of claim 7,
   wherein the gas flow partition includes a projecting part heading for the third dielectric substrate.

9. The gas processing apparatus of claim 7,
   wherein the second gap becomes narrow in a direction along the third plasma-induced flow.

10. The gas processing apparatus of claim 1, further comprising:
    a third dielectric substrate disposed on the first ground electrode;
    a fourth dielectric substrate facing the third dielectric substrate;
    a third and a fourth discharge electrode respectively disposed on a pair of facing principle surfaces of the third and fourth dielectric substrates; and
    a third ground electrode disposed on a principle surface at an opposite side of the principle surface of the fourth dielectric substrate,
    the AC power source being configured to generate a third plasma-induced flow at the third discharge electrode side and a fourth plasma-induced flow at the fourth discharge electrode side by applying the AC voltage between the third discharge electrode and the first ground electrode and between the fourth discharge electrode and the third ground electrode to ionize the gas mixture, the third and fourth plasma-induced flow including OH radical; and
    a second gap between the third and fourth dielectric substrates being 2 mm or more and 6 mm or less,
    wherein the object gas in the second gap is decomposed by the OH radical.

11. The gas processing apparatus of claim 10, further comprising:
    a switching mechanism configured to select one of or both of a group of the first and second discharge electrodes and a group of the third and fourth discharge electrodes, and to apply a high-voltage AC voltage.

* * * * *